US00PP11713P

United States Patent [19]

Heffner

[11] Patent Number: Plant 11,713

[45] Date of Patent: Dec. 19, 2000

[54] VARIETY OF PETUNIA NAMED 'TRUMPET PASTEL PINK'

[75] Inventor: Mike Heffner, Lompoc, Calif.

[73] Assignee: John Bodger and Sons Company, South El Monte, Calif.

[21] Appl. No.: 09/169,698

[22] Filed: Oct. 9, 1998

[51] Int. Cl.[7] ..... A01H 5/00

[52] U.S. Cl. ..... Plt./356

[58] Field of Search ..... Plt./356

[56] References Cited

U.S. PATENT DOCUMENTS

P.P. 8,489 12/1993 Hirabayashi et al. ..... Plt./356

P.P. 8,934 10/1994 Danziger ..... Plt./356

*Primary Examiner*—Bruce R. Campell
*Assistant Examiner*—Wendy A Baker
*Attorney, Agent, or Firm*—Fullwider Patton Lee & Utecht, LLP

[57] ABSTRACT

The claimed cultivar brings a new color to the Trumpet series of Petunias and is characterized by a large pink colored flower accented in its center with a large and distinctive green-white circular center, over medium green foliage. As with all Trumpet Petunias, this cultivar exhibits early flowering with superior branching so that the plant may also be used in a hanging pot.

1 Drawing Sheet

BACKGROUND OF THE NEW PLANT

The present invention relates to a new and distinct variety of Petunia known by the name 'Trumpet Pastel Pink' (Bodger No. 7P3361-1). The new variety was discovered in a selective breeding program by Mike Heffner at Bodger Seeds, Ltd., Lompoc, Calif. The new variety is a selection from the crossing of inventor's proprietary Petunia selection Bodger No. 7P6-0-3 (unpatented) which is a seedling with spreading decumbent habit and small pink colored flowers, with inventor's proprietary Petunia selection Bodger No. 71100-4 (unpatented) which is a seedling with upright habit and large light pink colored flowers.

This new variety is the result of a breeding program whose objective was to develop new vegetatively propagated petunias with a spreading cascading habit, large flowers and with a color range not presently available as a cutting product. The variety originated from a cross between two proprietary seedling selections taken from the existing breeding program. The progeny from this cross was grown out during the summer of 1997 and a number of single plants were selected as possible new varieties and propagated vegetatively. The cuttings were trialed and evaluated during winter and summer of 1998 at which time it was determined that this particular line, established from one single plant, was distinguishable and unique.

The new cultivar was first asexually reproduced by terminal vegetative cuttings at Bodger Seeds, Ltd., Lompoc, Calif. and has been repeatedly asexually reproduced by cuttings at Bodger Seeds Ltd., at Lompoc Calif. It has been found to be stable and true to type through successive propagations.

The new cultivar was grown in a glass greenhouse in Lompoc, Calif., using full light, 60° Fahrenheit night temperature, 77° Fahrenheit day temperature, and grown in soil having a temperature of 80° Fahrenheit. The claimed plant was grown from a terminal vegetative cutting, and exhibited an eight to ten weeks response time from an unrooted cutting to a 25 cm flowering plant.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Bodger Seeds Ltd., in Lompoc, Calif. The plant histories were taken on rooted cuttings believed to have been potted in a 25 cm pot, under full light in the greenhouse, and color readings were taken in day light using The Royal Horticultural Society of London Colour Chart.

THE PLANT

Classification:
- *Botanical.*—*Petunia×hybrida* Hort.
- *Commercial.*—Trumpet Pastel Pink petunia.

Form: Indeterminate with spreading and decumbent habit. When planted in a hanging pot the stems hang down.
- *Height.*—14.5 cm above the top of pot.
- *Spreading area of plant.*—74 cm in diameter.

Foliage: Moderate branching.

Leaves: Leaves are simple, opposite, occasionally whorled at base of stem; pinnate venation; foliage viscid; young stems soft, mature leaves more brittle; leaves horizontal to stem.
- *Size.*—5.2 cm length when fully expanded. 3.5 cm width when fully expanded. 1.0 mm thickness.
- *Shape.*—Broadly elliptic.
- *Margin.*—Entire.
- *Texture.*—Sparsely pubescent.
- *Color.*—Upper: Green Group 137B. Lower: Yellow-Green Group 147B.
- *Apex.*—Obtuse.
- *Base.*—Obtuse.

Stem:
- *General.*—Hanging; Spreading to a length of 37 cm.
- *Color.*—Yellow-Green Group 144B.
- *Internode length.*—2.1 cm .
- *Diameter.*—0.4 cm.
- *Anthocyanin pigmentation.*—Absent.
- *Texture.*—Pubescent.

INFLORESCENCE

Young flower:
*Diameter.*—5.8 cm.
*Length.*—4.3 cm.
*Color.*—Inside: Purple Group 75B, with a distinctive circular area in center of Greyed-Green Group 196D, center circular area 2.2 cm in diameter. Outside: Purple Group 75D with veins in Yellow-Green Group 145B.

Mature flower:
*Diameter.*—9.4 cm.
*Length.*—6.7 cm.
*Color.*—Inside: Purple Group 75B, with a distinctive circular area in center of Greyed-Green Group 196D, center circular area 2.2 cm in diameter. Outside: Purple Group 75D with veins in Yellow-Green Group 145B.

Open florets:
*Form.*—Single funnelform flowers; calyx five parted, petals united into flower tube; petal apex rounded to broadly acuminate.
*Texture and appearance.*—smooth on inside, pubescent on outside, presenting large pink flowers.

Pedicel:
*Length.*—3.8 cm.
*Thickness.*—0.4 cm.
*Texture.*—Pubescent.

Sepals:
*Quantity.*—5.
*Length.*—2.1 cm.
*Width.*—1.1 cm.
*Shape.*—Elliptic.
*Color.*—Inside: Green Group 137B. Outside: Green Group 137C.
*Apex.*—Obtuse.
*Margin.*—Entire.
*Texture.*—Pubescent.

Persistence:
*Disease resistance.*—No known special disease resistance compared with other Petunias.

REPRODUCTIVE ORGANS

Stamens:
*Number.*—5 normal stamens.
*Anthers.*—2 anthers level with stigma; 3 anthers below stigma; Yellow-White.
*Filaments.*—White.

Pistils:
*Number.*—1 normal.
*Stigma.*—Green.
*Style.*—Yellow-Green.

Ovaries: Superior.

GENERAL CHARACTERISTICS

'Trumpet Pastel Pink' brings a new and distinct color to the Trumpet Series of Petunias which is a group of varieties that are early flowering and very floriferous having large blooms over a medium green foliage. At maturity 'Trumpet Pastel Pink' has approximately 150–200 open blooms per 25 cm pot. 'Trumpet Pastel Pink' presents a large pink colored flower accented with a distinctive green-white circular center. The flowers open above the foliage and face outwards and have no fragrance. The variety shows normal fertility and seed set.

I claim:

1. A new and distinct variety of Petunia plant, substantially as shown and described.

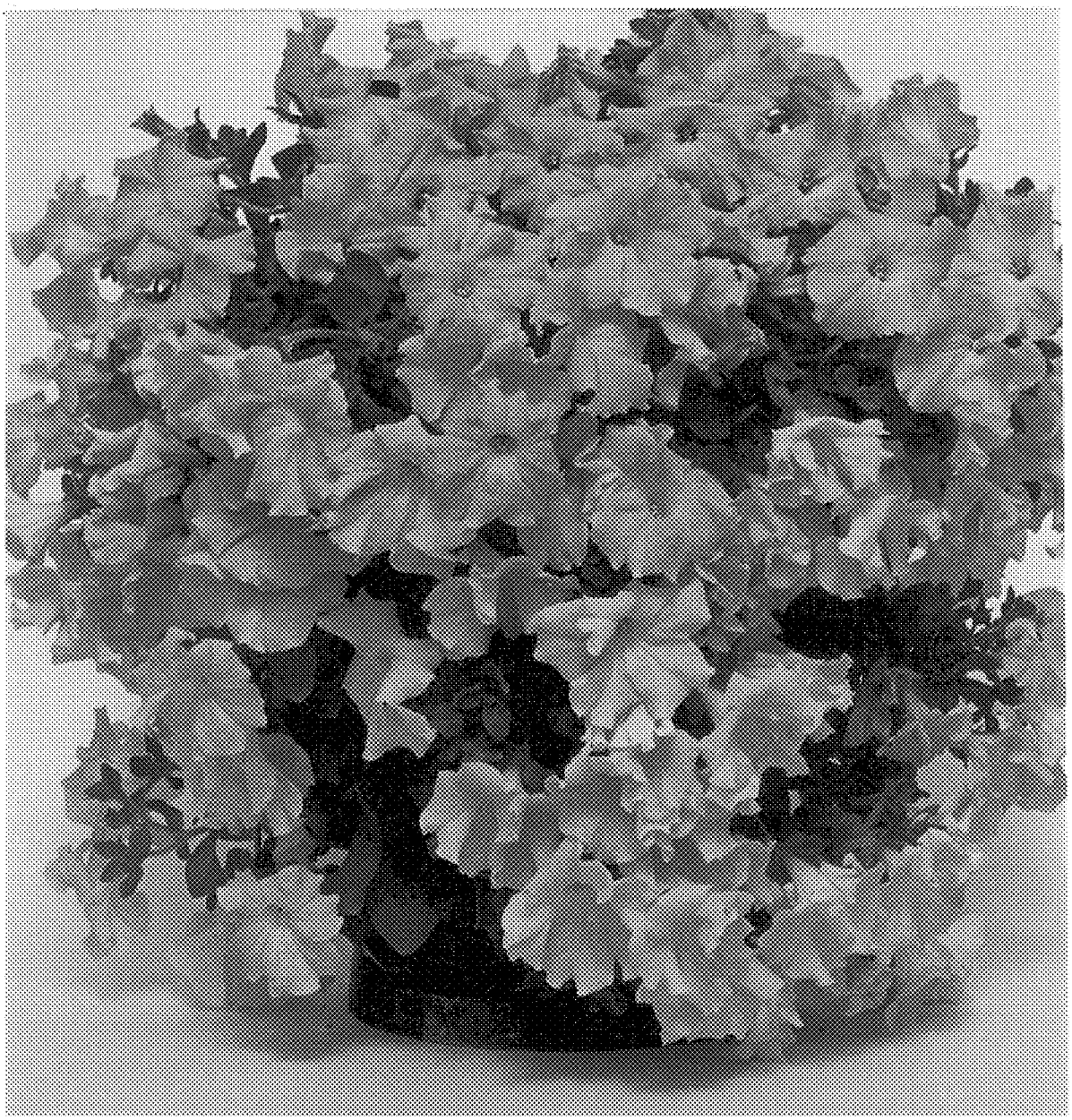

* * * * *